United States Patent [19]
Dahlen et al.

[11] 3,935,204
[45] Jan. 27, 1976

[54] CEPHALOSPORINS AND PHARMACEUTICAL PREPARATIONS CONTAINING THE SAME

[75] Inventors: Sven Erik Dahlén; Bertil Åke Ekström; Ödön Kálmán József Kovács; Berndt Olof Harald Sjöberg, all of Södertälje, Sweden

[73] Assignee: Astra Lakemedel Aktiebolag, Sodertalje, Sweden

[22] Filed: Mar. 13, 1973

[21] Appl. No.: 340,673

[30] Foreign Application Priority Data
Mar. 13, 1972 United Kingdom............... 11690/72

[52] U.S. Cl. ............................................. 424/246
[51] Int. Cl.² ........................................ A61K 31/51
[58] Field of Search.................. 424/246; 260/243 C

[56] References Cited
UNITED STATES PATENTS
3,692,779  9/1972  Holdrege ........................... 424/246

Primary Examiner—Jerome D. Goldberg
Attorney, Agent, or Firm—Brumbaugh, Graves, Donohue & Raymond

[57] ABSTRACT

New esters of cephalosporins of the formula

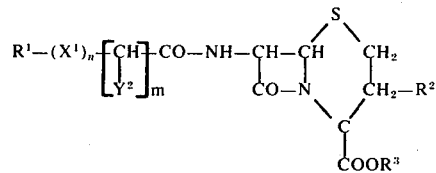

wherein $R^1$ is a substituted or unsubstituted alkyl, cycloalkyl, aryl or heterocyclic group, $R^2$ is $S-R^4$ wherein $R^4$ is a methyl, ethyl, benzyl or heterocyclic group, a xanthate, dithiocarbamate, thiouronium, azido, alkoxy, hydrogen, substituted or unsubstituted alkanoyloxy, carbonyloxy or 1-pyridinium group, $R^3$ is

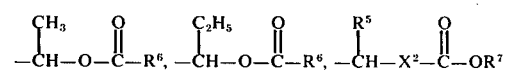

wherein $R^5$ is hydrogen, methyl or ethyl, $X^2$ is O or NH, $R^6$ is a basic group, $R^7$ is a substituted or unsubstituted alkyl, cycloalkyl, aryl, aralkyl or heterocyclic group, $X^1$ is O or S, $Y^1$ is hydrogen, a hydroxy, alkyloxycarbonyl, halogen, azido, a substituted or unsubstituted amino group, a carboxyl group, the group —COOR³, or a nitrite group, $n$ is 0 or 1 and $m$ is 0 or 1, useful as active ingredients of pharmaceutical preparations; processes for their preparation; and methods for the treatment of infectious diseases.

2 Claims, No Drawings

CEPHALOSPORIN AND PHARMACEUTICAL PREPARATIONS CONTAINING THE SAME

The present invention relates to new cephalosporins and methods for their preparation. The invention also relates to the preparation of pharmaceutical preparations containing the cephalosporine and to methods for the pharmacological use of the cephalosporins.

In particular this invention relates to new esters of cephalosporins of the general formula

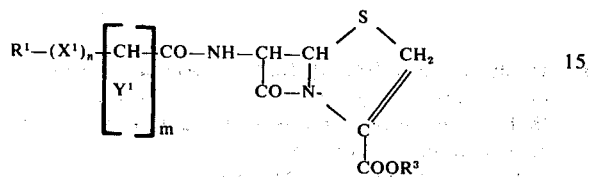

and pharmaceutically acceptable salts thereof, in which formula $R^1$ is selected from the group consisting of an alkyl group with 1–8 carbon atoms; a cycloalkyl group with 3–10 carbon atoms; an aryl group such as phenyl and naphthyl; a heterocyclic group such as thienyl, furyl, pyrazolyl, pyridinyl, oxazolyl, isoxazolyl, thiazolyl, isothiazolyl, thiadiazolyl, sydnonyl and tetrazolyl, wherein the alkyl, cycloalkyl, aryl and heterocyclic groups may be substituted with one or more groups selected from alkyl groups with 1–3 carbon atoms such as methyl, ethyl, propyl and isopropyl, halogen atoms such as chlorine, bromine, iodine and fluorine,
hydroxy groups,
nitro groups,
nitrile groups,
azido groups,
alkoxy groups with 1–3 carbon atoms such as methoxy, ethoxy, propoxy and isopropoxy,
carboxyl groups,
carboxymethyl groups and
carboxamidomethyl groups, $R^2$ is selected from the group consisting of a groups S—$R^4$ where $R^4$ is a methyl group, an ethyl group, a benzyl group or a heterocyclic group such as an imidazolyl, benzoimidazolyl, benzothidazolyl, benzoaximidmazlyl, benzoimidazolyl, benzothiazolyl, benzoxazolyl or thiadiazolyl group;
a xanthate group;
a dithiocarbamate group such as a dimethyl, piperidyl, 4-akylpiperazido or 4-dialkylpiperazonium dithiocarbamate group;
a thiouronium group;
an azido group;
an alkoxy group with 1–4 carbon atoms such as a methyl, ethyl, propyl, isopropyl, butyl, sec.butyl or tertiary butyl group;
a hydrogen atom;

an alkanoyloxy group such as acetoxy and propionyloxy;
a carbonyloxy group such as methylaminocarbonyloxy;
1-pyridinium;
and wherein the alkanoyloxy, carbonyloxy and 1-pyridinium groups may be substituted with one or more groups selected from
alkyl groups with 1–3 carbon atoms such as methyl, ethyl, propyl and isopropyl,
halogen atoms such as chlorine, bromine, iodine and fluorine,
hydroxy groups,
nitrile groups,
hydroxymethyl groups,
alkoxycarbonyl groups,
aminocarbonyl groups;

$R^3$ is selected from the group consisting of

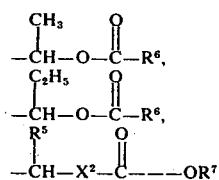

wherein
$R^5$ is a hydrogen atom, a methyl or an ethyl group;
$X^2$ is O, NH;
$R^6$ is a basic group such as alkyl or aralkyl substituted with substituted or unsubstituted $NH_2$, such as alkyl-$NHCH_3$, aralkyl-$NHCH_3$,

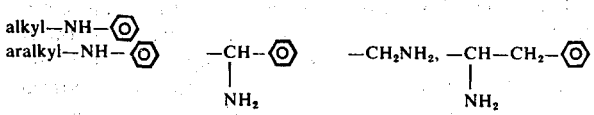

$R^7$ is an alkyl group such as a methyl, ethyl, propyl, isopropyl, butyl, isobutyl, pentyl or 2-ethyl-hexyl group;
a cycloalkyl group such as cyclopropyl, cyclobutyl, cyclopentyl, cyclohexyl or cycloheptyl;
an aryl group such as phenyl or naphtyl;
an aralkyl group such as benzyl or naphthylmethyl;
a heterocyclic group and wherein the alkyl, cycloalkyl, aryl, aralkyl and heterocyclic groups may be substituted with one or more groups selected from the class consisting of aminio groups, substituted amino groups such as methylamino, diethylamino or acetamido groups,
the halogen groups such as fluorine, chlorine or bromine, nitro groups,
alkoxy groups such as methoxy, ethoxy, propyloxy, isopropyloxy, butoxy or isobutoxy; and
$X^1$ is selected from the group consisting of O and S;
$Y^1$ is selected from the group consisting of
a hydrogen atom;
a hydroxy group;
an alkyloxycarbonyl group such as methoxycarbonyl;
a halogen group such as bromine, chlorine, fluorine or iodine;
and azido group;
an amino group;

a substituted amino group such as methylamino, diethylamino, benzyl sulphenylamino, methoxy-(hydroxy)phosphinylamino and acetamido;
a carboxyl group or the group —COOR³, wherein R³ is as defined above, and a nitrile group;
n is 0 or 1,
m is 0 or 1.

Illustrative examples of radicals included in the above definitions and in the definitions throughout the application are:

alkyl: methyl, ethyl, propyl, isopropyl, butyl, isobutyl, pentyl, hexyl, heptyl, octyl, 2-ethyl-hexyl
cycloalkyl: cyclopropyl, cyclobutyl, cyclopentyl, cyclohexyl, cycloheptyl
alkoxy: methoxy, ethoxy, propyloxy, isopropyloxy, butoxy, isobutoxy
halogen: F, Cl, Br
aryl: phenyl, naphthyl naphthylmethyl, indanyl
aralkyl: benzyl, naphthylmethyl
heterocyclic groups:

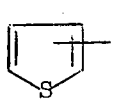 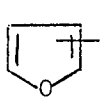 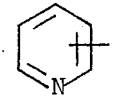 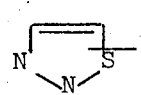

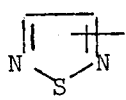 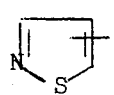 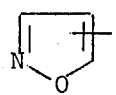 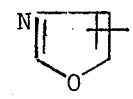 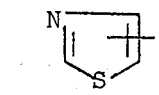

The above illustrative examples illustrate, where applicable, all the radicals so far mentioned and other radicals appearing hereafter in the application of the extent of the definition given to each radical and within the boundaries with regard to number of carbon atoms, which may be prescribed for each radical.

The invention relates in a further aspect to such chemical intermediates which are new and useful in the preparation of the compounds of the formula I.

The compounds of the invention are of value in the treatment of infectious diseases in man or animal caused by bacterial organisms. They may be isolated and used as such but also, depending on the presence of basic or acidic groups in the molecule, in the form of salts with pharmaceutically acceptable organic or inorganic acids or bases. Examples of suitable acids are hydrochloric acid, citric acid, and fumaric acid. Examples of suitable bases are sodium hydroxide, potassium hydroxide, calcuim hydroxide, aluminium hydroxide, ammonium hydroxide, non-toxic amines as trialkylamines, including triethylamine, procaine, dibenzylamine, N-benzyl-β-phenethylamine, 1-ephenamine, N,N¹-dibenzylethylenediamine, dehydroabiethylamine, N,N¹-bis-dehydroabiethylethylenediamine, N-(lower-)alkylpiperidine (e.g. N-ethyl-piperidine) and other bases which have been used for the preparation of salts with cephalosporins.

The side chain of the cephalosporin structure in formula I may contain an asymmetric carbon atom in the α-position. Depending on the configuration around this carbon atom the compound will occur in two different diastereoisomeric forms which are both biologically active. Likewise the ester groups may contain asymmetric atoms, e.g. when R³ is

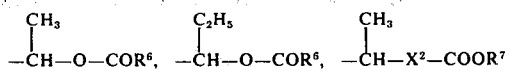

or —CH—X²—COOR⁷ giving rise to different diastereoisomeric forms which also all are biologically active. It is to be understood that the invention comprises the pure diastereoisomers as well as mixtures of them.

It is known that cephalosporins of the general structure (II):

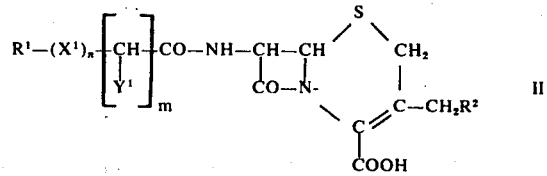

or salt thereof, where R¹, R², X¹, Y¹, m and n are as defined above, have good antibacterial activity against grampositive and gramnegative bacteria, including penicillinase producing staphylococci.

compounds of the general formula II are, however, poorly absorbed when administered orally and the compounds have in general to be given by injection. It is one purpose of the present invention to provide esters of these compounds, which are well absorbed orally and then hydrolyzed within the body to give blood and organ levels of the compounds of the general formula II that are adequate for the treatment of infectious diseases, caused by bacteria sensitive to cephalosporins of the general formula II. To achieve the full antibacterial activity of the cephalosporins with general formula II it is necessary to choose such ester groups that are rapidly hydrolysed in vivo with release of the cephalosporins of the general formula II. It is an essential feature of the present invention to provide such ester groups that are rapidly hydrolysed in the body after oral absorption.

Said compounds having the formula I are well tolerated, give a low frequency of side-effects and may readily be used in pharmaceutical preparations, either as such or in the form of their salts, and they can be intermxied with solid carriers or adjuvants or both. In such preparations the ratio between the therapeutic substance and the carriers and adjuvants may vary between 1 and 95 %. The preparation may either be processed to for instance tablets, pills or dragées or can be supplied to medical containers, such as capsules or as regards mixtures they can be filled on bottles. Pharmaceutically acceptable, organic or inorganic, solid or liquid carriers may be used, suitably for oral or enteral administration or for topical application, in manufacturing the preparations. Gelatine, lactose, starch, magnesium stearate, talc, vegetabilic and animalic fats and oils, vegetabilic rubber and polyalkylene glycol and other known carriers for pharmaceuticals are all suitable for manufacturing preparations of said compounds. Moreover, the preparation may contain other pharmaceutical active components, being suitably admimistratable together with the compounds of the invention when treating infectious diseases. For instance other suitable antibiotical substances, e.g. gentamycin and polymycin.

In the treatment of bacterial infections in man, the compounds of invention are for example administered in amounts corresponding to 5 to 200 mg/kg/day, preferably in the range of 10 to 100 mg/kg/day in divided dosages, e.g. two, three or four times a day. They are adminstered in dosage units containing e.g. 175, 350, 500 and 1000 mg of the compounds.

Preferred classes of compounds of the invention are such compounds of formula I, where $R^3$ is selected from the group consisting of lower alkoxycarbonyloxymethyl, 1'-lower alkoxycarbonyloxyethyl, 1'-lower alkoxycarbonyloxypropyl, lower alkoxycarbonylaminomethyl, 1'-lower alkoxycarbonylaminoethyl, 1'-lower alkoxycarbonylaminopropyl, amino-substituted 1'-lower acyloxyethyl, amino-substituted 1'-lower acyloxypropyl, phenoxycarbonyl oxymethyl, 5-indanyloxymethyl, 1'-phenoxycarbonyloxyethyl, 1'-(5-indanyloxy)carbonyloxyethyl.

Further classes of preferred compounds are obtained by substituting the acyloxy moieties or the alkoxycarbonyloxy, the acyloxycarbonyloxy, the alkyloxycarbonylamino or the acyloxycarbonylamino groups in $R^3$ with amino, methylamino or di (lower) alkylamino groups.

Examples of suitable and preferred compounds of the invention are given in the table below.

Table $$R^1-(X^1)_n-\underset{\underset{Y^1}{|}}{CH}-CO-NH-\underset{\underset{\underset{\underset{COOR_3}{|}}{N}}{|}}{CH}-CH\diagup\overset{S}{\diagdown}CH_2-R^2$$

| $R^1$ | $X^1$ | n | $Y^1$ | $R^2$ | $R^3$ |
|---|---|---|---|---|---|
| $C_6H_{13}$ | O | | H | $OCOCH_3$ | $-CH_2OCOOC_2H_5$ |
| $C_6H_5$ | O | | H | $OCOCH_3$ | $-CH_2OCOOC_2H_5$ |
| $C_6H_5$ | O | | H | $OCOCH_3$ | $-\underset{\underset{CH_3}{|}}{CH}-OCOOC_2H_5$ |
| $C_6H_5$ | O | | H | $OCOCH_3$ | $-\underset{\underset{C_2H_5}{|}}{CH}-OCOOC_3H_7$ |
| $C_6H_5$ | O | | H | $OCOCH_3$ | $-CH_2NH-COOC_2H_5$ |
| $C_6H_5$ | O | | H | $OCOCH_3$ | $-CH_2-OCOOCH_2CH_2NH_2$ |
| $m$-Br-$C_6H_4$ | O | | H | $OCOCH_3$ | $-CH_2OCOOC_2H_5$ |
| $C_{10}H_8$ | O | | H | $OCOCH_3$ | $-\underset{\underset{CH_3}{|}}{CH}-OCOOC_2H_5$ |
|  | O | | H | $OCOCH_3$ | $-CH_2OCOOC_2H_5$ |
|  | O | | H | $OCOCH_3$ | $-\underset{\underset{CH_3}{|}}{CH}-OCOOC_2H_5$ |
|  | O | | H | $OCOCH_3$ | $-\underset{\underset{CH_3}{|}}{CH}-OCOOCH_2CH_2NH-CH_3$ |
|  | O | | H | $OCOC_6H_5$ | $-CH_2-OCOOC_2H_5$ |

Table-continued $$R^1-(X^1)_n-\underset{\underset{Y^1}{|}}{CH}-CO-NH-\underset{\underset{CO-N}{|}}{CH}-CH\underset{\underset{COOR_3}{|}}{\overset{S}{\diagup}}CH_2-R^2$$

| R¹ | X¹ | n | Y¹ | R² | R³ |
|---|---|---|---|---|---|
| 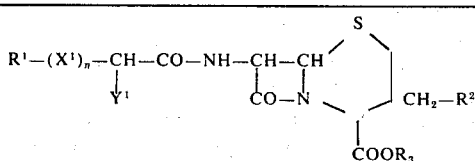 | | O | H | OCOCH₃ | —CH₂OCOOC₂H₅ |
| Cl(CH₂)₄ | | O | H | OCOCH₃ | —CH₂OCOOC₆H₅ |
| C₆H₅ | O | 1 | H | OCOCH₃ | $\underset{\underset{}{}}{\overset{CH_3}{|}}$ CH—OCOOC₂H₅ |
| C₆H₅ | S | 1 | H | OCOCH₃ | —CH₂—OCOOC₂H₅ |
| C₆H₅ | S | 1 | H | OCOCH₃ | $\overset{CH_3}{|}$ —CH—OCOOCH₂CH₂—NH—CH₃ |
|  | S | 1 | H | OCOCH₃ | —CH₂—OCOOC₂H₅ |
|  | S | 1 | H | OCOCH₃ | —CH₂—OCOOCH₂ CH₂ NH₂ |
| C₆H₅ | | O | N₃ | OCOCH₃ | —CH₂—OCOOC₂H₅ |
| C₆H₅ | | O | N₃ | OCOCH₃ | $\overset{CH_3}{|}$ —CH—OCOOC₂H₅ |
| C₆H₅ | | O | NH₂ | OCOCH₃ | —CH₂—OCOOC₂H₅ |
| C₆H₅ | | O | NH₂ | OCOCH₃ | $\overset{CH_3}{|}$ —CH—OCOOC₂H₅ |
| C₆H₅ | | O | NH₂ | OCOCH₃ | $\overset{C_2H_5}{|}$ —CH—OCOOC₃H₇ |
| C₆H₅ | | O | NH₂ | OCOCH₃ | —CH₂—OCOOC₆H₅ |
| C₆H₅ | | O | NH₂ | OCOCH₃ | 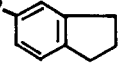 |
| C₆H₅ | | O | —COOH | OCOCH₃ | —CH₂—OCOOC₂H₅ |
| C₆H₅ | | O | OH | OCOCH₃ | —CH₂—OCOOC₂H₅ |
| C₆H₅ | | O | OH | OCOCH₃ | $\overset{CH_3}{|}$ —CH—OCOOC₂H₅ |
| C₆H₅ | | O | OH | OCOCH₃ | $\overset{CH_3}{|}$ —CH—OCOCH₃ |
| C₆H₅ | | O | OH | OCOCH₃ | —CH₂—OCOOCH₂CH₂NH₂ |
| C₆H₅ | | O | OH | OCOCH₃ | —CH₂—OCOOC₆H₅ |
|  | | O | H |  | —CH₂—OCOOC₂H₅ |
|  | | O | H |  | $\overset{CH_3}{|}$ CH—OCOOC₂H₅ |

Table-continued $$R^1-(X^1)_n-\underset{Y^1}{CH}-CO-NH-CH-CH\underset{COOR_3}{\overset{S}{\underset{|}{\diagdown}}}CH_2-R^2$$

| R¹ | X¹ | n | Y¹ | R² | R³ |
|---|---|---|---|---|---|
| thienyl | | O | H | —N(+)-pyridyl | CH₃–CH–OCOCH₃ |
| thienyl | | O | H | —N(+)-pyridyl | CH₂—NHCOOC₂H₅ |
| thienyl | | O | H | —N(+)-pyridyl | CH₂—OCOOCH₂CH₂NH₂ |
| thienyl | | O | H | SCH₂C₆H₅ | —CH₂OCOOC₂H₅ |
| thienyl | | O | H | N-piperazinyl-N(+)-CH₃ | CH₃–CH–OCOOC₂H₅ |
| thienyl | | O | H | —S—CS—N(CH₃)₂ | —CH₂—OCOOCH₂CH₂NHCH₃ |
| thienyl | | O | H | —S—C(=NH₂(+))NH₂ | —CH₂—OCOOC₂H₅ |
| thienyl | | O | H | —N₃ | —CH₂—OCOOC₂H₅ |
| tetrazolyl-CH | | O | H | —S-(5-methyl-1,3,4-thiadiazol-2-yl) | —CH₂—OCOOC₂H₅ |
| tetrazolyl-CH | | O | H | —S-(5-methyl-1,3,4-thiadiazol-2-yl) | —CH₂—OCOOCH₂CH₂NH₂ |
| thienyl | | O | H | —N(+)-(3-Cl-pyridyl) | —CH₂—OCOOC₂H₅ |
| phenyl | | O | NH₂ | H | —CH₂—OCOOC₂H₅ |
| phenyl | | O | NH₂ | H | —CH(CH₃)—OCOOC₂H₅ |
| phenyl | | O | NH₂ | H | —CH₂—NH—COOC₂H₅ |

The compounds of the invention are prepared by different methods.

METHOD A

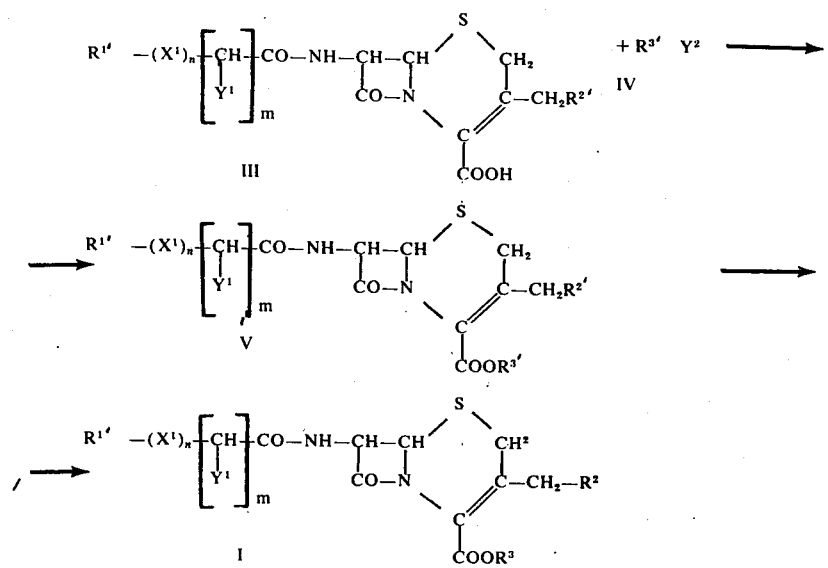

In the formulas above $R^1$, $R^2$, $R^3$, $X^2$, $m$, $n$ and $Y^1$ have the meaning given above and $R^{1'}$, $R^{2'}$, $R^{3'}$ and $Y^{1'}$ are $R^1$, $R^2$, $R^3$ and $Y^1$ respectively or in case these latter groups contain amino or carboxy groups protected derivatives of these. $Y^2$ is a halogen group, preferably chlorine, bromine or iodine group or a functionally equivalent group such as an organic sulphonic acid residue.

According to this method a cephalosporin of the general formula III, preferably in the form of its salt, e.g. the sodium, potassium, calcium, triethylammonium or tetraalkylammonium salt, is brought to react with a compound $R^3Y^2$ to give a compound of the formula V.

The reaction is preferably performed in an organic solvent like acetone, tetrahydrofurane, chloroform, methylene chloride, dimethylformamide, dimethylsulphoxide or hexamethylphosphoramide or in a mixture of water and an organic solvent, e.g. aqueous dioxane or acetone.

When $R^{1'}$, $R^{2'}$, $R^{3'}$ and $Y^{1'}$ are $R_1$, $R_2$, $R_3$ and $Y_1$ respectively the compounds of formula V belong to the compounds of the invention of the general formula I. When they contain amino or carboxyl groups that are protected the protecting groups can be removed in manners known to the art in at least one additional step to give compounds of the general formula I. As protecting groups such can be used that can be removed without destruction of the cephalosporin ring system.

Such protecting groups are known to the art and may be represented e.g. by the benzyloxycarbonyl, the o-nitrophenylsulphenyl, the 2-p-tolysulphonyl-ethoxycarbonyl, the β-trichloroethoxycarbonyl and 1-methoxycarbonylpropen-2-yl group as protecting groups for amino groups and e.g. by the benzyl, the β-trichloroethyl or the 2,6-dichlorobenzyl groups for the protection of carboxy groups. To obtain amino cephalosporin esters of the general formula I may further the corresponding azido or nitro compounds which also belong to the compounds of the general formula I be reduced e.g. by catalytic hydrogenation.

METHOD B

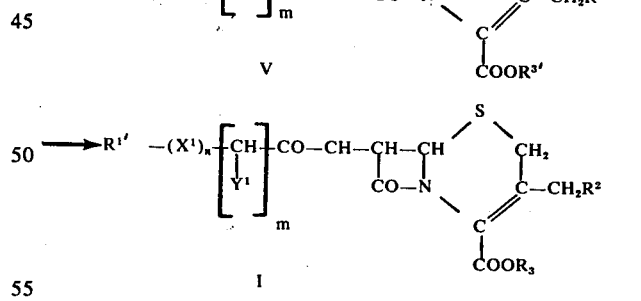

According to this method an activated carboxylic acid derivative VI where $X^1$, $R^{2'}$, $m$ and $Y^{1'}$ are as defined in method A and —CO—Z is a reactive group capable of reacting with an amino group under formation of an amide moiety, e.g. an acid chloride or its functional equivalent is brought to react with a compound of formula VII, where $R^{2'}$ and $R^{3'}$ are as defined previously to give the cephalosporin ester V. As outlined in method A this compound is either a compound of the invention of the general formula I or may be converted into such a compound by removal of the protecting groups.

The reaction between VI and VII constitutes an acylation and can be performed in the manner described for acylation of esters of 7-aminocephalosporanic acids. The acylating group CO—Z in VI may be an acid chloride group, or a group functioning in the same way, e.g. an acid bromide, an acid azide, an anhydride, a mixed anhydride formed with an inorganic acid or an organic acid such as an alkyl carbonic acid, for instance isobutyl carbonic acid, a carbonic acid, a sulphonic acid and especially an alkoxyformic acid or may be a radical obtained by reacting the α-substituted phenylacetic acid and a carbodiimide or N,N¹-carbonyldiimidazol or an other compound reacting in a similar way. The reaction can be performed in organic solvents like diethylether, tetrahydrofurane, acetone, ethyl acetate, chloroform, methylene chloride, dimethylformamide, dimethylsulphoxide or hexamethylphosphoramide, in water or in aqueous organic solvents in presence of organic or inorganic bases like triethylamine, quinoline, pyridine, N-methyl-morpholine, sodium hydroxide, sodium bicarbonate or potassium carbonate.

The esters of the general structure VII may be prepared by treatment of salts of the corresponding acids ($R^{3'}$=H) with compounds $R^{3'}$—$Y^2$, where $R^{3'}$ and $Y^2$ have the same meaning as above. The reaction is preferably performed in organic solvents like dimethylformamide, dimethylsulphoxide or hexamethylphosphoramide.

Alternatively 7-acylated derivatives of the compounds of the formula

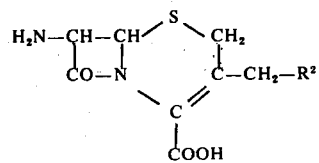

wherein $R^2$ has the meaning given above, with acyl groups that can be removed without destruction of the cephem ring system are treated with $R^3$ —$Y^2$ to give esters of the cephem structure from which the acyl groups then are removed to give the esters of the formula VII. One method consists of reacting a salt, e.g. the sodium, potassium or tetraalkylammonium salt of the compound of the formula

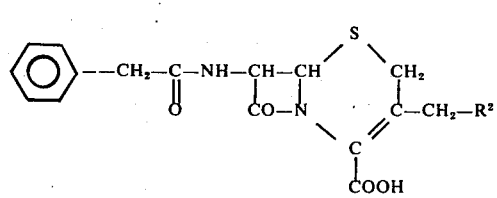

wherein $R^{2'}$ has the meaning given above, with $R^{3'}$—$Y^2$ in an organic solvent like acetone, methylethylketon, chloroform, methylene chloride, dimethylformamide, dimethylsulphoxide or hexamethylphosphoramide or in a mixture of an organic solvent and water, e.g. aqueous acetone or dioxane to give the corresponding ester. The phenylacetyl side chain is then removed according to the method described in Neth. Pat. specification No. 6,401,421 or South African Pat. specification No. 67/2927 by treatment with phosphorous pentachloride in presence of a tertiary organic base to give an imino chloride which is reacted with an alcohol like propanol to give the corresponding imino ether which is hydrolyzed by addition of water or alcoholized by addition of alcohol to give the ester VII. Alternatively the phenylacetyl side chain may be removed by enzymatic hydrolysis using an E.coli acylase in analogy to method described in French Pat. specification No. 1,576,027.

In still another method N-protected derivatives of the compounds of the formula

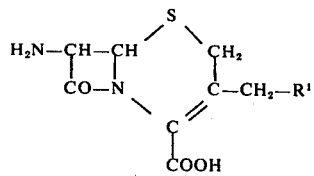

wherein $R^2$ has the meaning given above, are reacted with $R^3$ —$Y^2$ to give the corresponding ester from which the protecting groups are removed to give the compounds of the general formula VII. Examples of protecting groups which can be used are the benzyloxycarbonyl group which is removed by catalytic hydrogenation, the o-nitrophenylsulphenyl group which can be removed by treatment with nucleophilic agents at acid pH (Japanese patent specification 505, 176) and the trityl group which can be removed by mild acid hydrolysis.

METHOD C

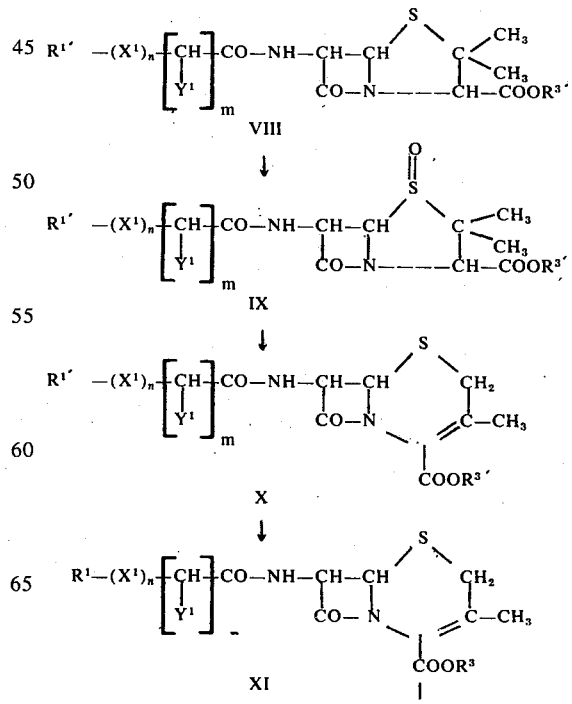

In the formulas above $R^1$, $R^3$, $X^1$, $m$, $n$ and $Y^2$ have the meaning given above.

When $R^2$ of the formula I is hydrogen the compounds of the invention may be prepared from the corresponding penicillin esters (VIII).

By known methods, e.g. by oxidation with hydrogen peroxide or by a peracid, the penicillin esters are converted into the corresponding sulphoxides (IX), which by treatment e.g. with acid catalysts, e.g. p-toluenesulphonic acid in xylene or with an acid, an anhydride e.g. acetic anhydride or with an organic phosphoric acid in presence of an organic base or a phosphonate salt, e.g. pyridinium phosphate are converted into the cephalosporin esters X, which either are compounds of the invention within the formula I or may be converted into such as described in Method A and B.

METHOD D

According to this method the carboxylic group in the 4-position of a natural cephalosporin or a functional derivative thereof is esterified by reaction with a compound of the formula $R^3$ -$Y^2$, wherein $R^3$ and $Y^2$ have the meanings specified above, whereafter the compound thus formed is transformed, according to the method described in the Belgian Pat. specification No. 628,494, to an imino ether by reaction with for instance a trialkyl-oxonium-fluoborate, whereafter the thus obtained imino ether is reacted with a compound of the formula

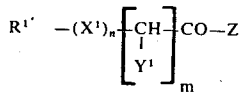

wherein $R^1$, $X^1$, $Y^1$; m, n and Z have the meanings given above and whereafter the reaction product is hydrolyzed in a conventional manner to the compound of the formula

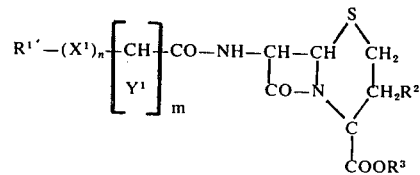

which compound is converted into a compound of the formula I as described under Method A above.

In this method the acylation step may take place without isolation of the intermediate imino ether. Alternatively the imino-ether may be obtained by reacting the cephalosporins with a halogenating agent like phosphorous pentachloride followed by an alcohol like metanol.

The preferred natural cephalosporin is cephalosporin C and its derivatives. Alternatively a semisynthetic cephalosporin may be used as starting material.

As described above the starting material may be in the form of a salt, for instance a sodium, potassium, calcium or trialkylammonium salt, in some of the ways for the preparation of the compounds of the invention.

In addition, tetraalkylammonium salts and other analogous salts such as salts where the cation has the formula $$A^1A^2A^3A^4N^+$$

in which formula $A^1$ is selected from the group consisting of straight and branched alkyl groups containing from 3 to 6 carbon atoms, substituted and unsubstituted aryl, and substituted and unsubstituted aralkyl, and wherein $A^2$, $A^3$ and $A^4$, which are the same or different, are selected from the group consisting of straight and branched alkyl groups containing from 1 to 6 carbon atoms, provided that $A^2$, $A^3$ and $A^4$ are alkyl with 3-6 carbon atoms when $A^1$ is alkyl, may be used.

Illustrative examples of suitable combinations of $A^1$, $A^2$, $A^3$ and $A^4$ in the quaternary ammonium ion $A^1A^2A^3A^4N^+$ are given below:

TABLE I.

Examples of suitable combinations of the radicals $A^1$–$A^4$ in the $A^1A^2A^3A^4N^+$ ion

| $A^1$ | $A^2$ | $A^3$ | $A^4$ |
|---|---|---|---|
| n-propyl | n-propyl | n-propyl | n-propyl |
| i-propyl | i-propyl | i-propyl | i-propyl |
| n-butyl | n-butyl | n-butyl | n-butyl |
| i-butyl | i-butyl | i-butyl | i-butyl |
| n-pentyl | n-pentyl | n-pentyl | n-pentyl |
| n-hexyl | n-hexyl | n-hexyl | n-hexyl |
| phenyl | methyl | methyl | methyl |
| phenyl | ethyl | ethyl | ethyl |
| p-tolyl | ethyl | ethyl | ethyl |
| p-chlorophenyl | ethyl | ethyl | ethyl |

When the radicals $A^1$–$A^4$ all are different the resulting ion contains an asymmetric centre and may occur in two enantiomeric forms. Epimeric forms can occur if $A^1$, $A^2$, $A^3$ and/or $A^4$ contain one or more asymmetric carbon atoms.

Examples of quaternary ammonium ions containing an asymmetric centre are given in Table II below:

TABLE II.

Examples of quaternary ammonium ion $A^1A^2A^3A^4N^+$ containing an asymmetric centre

| $A^1$ | $A^2$ | $A^3$ | $A^4$ |
|---|---|---|---|
| benzyl | n-propyl | i-propyl | n-butyl |
| benzyl | n-propyl | i-propyl | sec.butyl |
| benzyl | n-propyl | n-butyl | sec.butyl |
| n-propyl | n-propyl | n-butyl | sec.butyl |
| n-propyl | n-propyl | n-propyl | sec.butyl |
| n-propyl | n-propyl | n-propyl | sec.pentyl |
| n-propyl | n-propyl | n-propyl | sec.hexyl |
| n-propyl | n-propyl | n-butyl | sec.hexyl |

The use as described above of a quaternary salt form of the starting material for the preparation of the compounds of this invention is not previously described in the literature pertaining to this technical field. In this method the preferred cation is the tetraalkylammonium ion, particularly the tetrabutylammonium ion. The preferred solvents are chloroform, methylenechloride and acetone.

The quaternary ammonium salt form of the above described starting material may be prepared by reacting the starting material in question with a quaternary ammonium salt of the formula $A^1A^2A^3A^4N^+ B^-$ wherein $A^1$, $A^2$, $A^3$ and $A^4$ have the meanings specified above and B is a suitable anion such as $HSO_4^-$, $Cl^-$ or $CH_3COO^-$ to the formation of a quaternary salt of the starting material.

The salts of the formula above which contain B as the anion may be prepared in known manner analogously as described in for instance Belgian patent 751,791. The anion $B^-$ is in the preferred embodiment $HSO_4^-$.

7-acylamino-$\Delta^3$-cephem-4-carboxylic acid esters may partly rearrange into the corresponding ester of $\Delta^2$-cephem-4-carboxylic acids which have less antibacterial activity than the corresponding $\Delta^3$ compounds. The presence of such esters may be detected with the aid of UV, IR and NMR spectroscopy. In cases where such $\Delta^2$-ester occur they may be converted into the desired $\Delta^3$-esters by methods known to the art, e.g. by oxidising the $\Delta^2$-ester to a sulphoxide, treating this with acetyl chloride and reducing it, e.g. with sodium dithionite to give the $\Delta^3$-ester. Alternatively the $\Delta^2$ and $\Delta^3$-esters may be separated from each other, e.g. by chromatography.

The following examples will further illustrate the invention.

EXAMPLE 1

Ethoxycarbonyloxymethyl 7(2-thienylacetamido)-cephalosporanate

To a stirred suspension of sodium 7(2-thienylacetamido)-cephalosporanate (2.5 g, 6.0 mmole) in dimethylformamide (25 ml) was added chloromethylethylcarbonate (1.66 g, 12.0 mmole). After stirring at room temperature for 23 hours the mixture was poured into a mixture of ethylacetate and water. The organic phase was washed with saturated sodium bicarbonate and brine, dried and evaporated in vacuo to give a solid which was washed repeatedly with petroleum ether to remove excess of chloromethylethylcarbonate. The residue was dried to give 1.2 g of a gray solid, m.p. 107°–111°C. The product showed strong IR-absorption at 1785–1750 $cm^{-1}$ indicating the presence of $\beta$-lactam and ester carbonyls.

The product was dissolved in methylenechloride (75 ml). The stirred solution was cooled in ice while 90% m-chloroperbenzoic acid (1.1 g. 5.75 mmole) in methylene chloride (50 ml) was added during 10 minutes. After stirring at room temperature for 3 hours the mixture was washed with saturated sodium bicarbonate and brine, dried and evaporated in vacuo to give an oil (0.7 g) which crystallized on standing, m.p. 120°–130°C.

Sodium dithionite (0.4 g, 2.3 mmole) was added to a stirred solution of ethoxycarbonyloxymethyl 7-(2-thienylacetamido)-cephalosporanate sulphoxide (0.7 g, 1.4 mmole) in dimethylformamide (10 ml). The mixture was cooled on ice while acetylchloride (4.5 g, 58 mmole) was added during 10 minutes and for a further 30 minutes. The suspension was poured into saturated sodium bicarbonate and extracted with ethylacetate. The organic phase was washed with water and brine, dried and evaporated in vacuo to give the ethoxycarbonyloxymethyl 7-(2-thienylacetamido)-cephalosporanate as 0.3 g of an oil which crystallized on standing. The product showed strong IR-absorption at 1780–1750 $cm^{-1}$ indicating the presence of $\beta$-lactam and ester carbonyls. It was found to be rapidly hydrolysed by human serum.

In the same way ethoxycarbonylaminomethyl 7-(3-thienylacetamido-cephalosporanate, (2-methyl-1,3-dioxen-5-yl)oxycarbonyloxymethyl 7-(m-chlorophenylacetamido-cephalosporanate, 1′-(2″-N-benzyloxycarbonyl-methylamino)-ethoxycarbonyloxyethyl 7-(2-thienylacetamido)-cephalosporanate could be prepared.

EXAMPLE 2

Ethoxycarbonyloxymethyl 7-(D-α-azidophenylacetamido)-cephalosporanate

Chloromethylethylcarbonate (1.77 g, 12.8 mmole) was added to a stirred suspension of potassium 7-(D-α-azidophenylacetamido)-cephalosporanate (3.0 g, 6.4 mmole) in dimethylformamide (25 ml) at room temperature. The reaction mixture was stirred for 23 hours and then diluted with ethylacetate. The solution was washed successively with water, aqueous sodium bicarbonate and brine, dried and evaporated in vacuo at 30°C. The residue was washed repeatedly by decantation with petroleum ether to remove excess or chloromethylethylcarbonate. The resulting yellowish gum (0.4 g) was dissolved in chloroform (75 ml) and chilled to 0°C. To the cold, stirred solution 90% m-chlorobenzoic acid (1.1 g, 5.75 mmole) in chloroform (50 ml) was added during $-¾$ minutes. After stirring at room temperature for 3 hours the mixture was washed with saturated sodium bicarbonate and brine, dried and evaporated in vacuo to give a yellow solid (0.5 g).

Sodium dithionite (0.4 g, 2.3 mmole) was added to a stirred solution of ethoxycarbonyloxymethyl 7-(D-α-azidophenylacetamido)-cephalosporanate sulphoxide (0.4 g, 0.73 mmole) in dimethylformamide (10 ml). The mixture was cooled on ice while acetylchloride (2.67 g, 34 mmole) was added during 10 minutes and for a further 30 minutes. The suspension was poured into saturated sodium bicarbonate and extracted with ethylacetate. The organic phase was washed with water and brine, dried and evaporated in vacuo to give 0.1 g of a yellowish oil. The product showed strong IR-absorption at 2120 and 1785–1750 $cm^{+1}$ indicating the presence of an azido group, a $\beta$-lactam ring and ester carbonyls respectively, and was found to be rapidly hydrolysed to the corresponding cephalosporanic acid in presence of human serum.

In the same way phenoxycarbonyloxymethyl 7-(azidoacetamido)-cephalosporanate, phenoxycarbonyloxymethyl 7-(cyclohexylacetamido)-cephalosporanate and 7-(2-thienylacetamido)-3-azidomethylcephem, ethoxycarbonyloxymethyl ester, ethoxycarbonyloxyethyl 7-(sydnonyl-3-acetamido)-cephalosporanate and ethoxycarbonyloxethyl 7-(sydnonyl-3-acetamido)-3-(5′-methyl-thiodiazolyl-thiomethyl)-cephem-4-carboxylate could be prepared.

EXAMPLE 3

Ethoxycarbonyloxymethyl 7-(D-α-aminophenylacetamido-cephalosporanate hydrochloride Ethoxycarbonyloxymethyl 7-(D-α-azidophenylacetamido)-cephalosporanate (0.1 g, 0.19 mmole) in ethylacetate (25 ml) was hydrogenated for 4 hours over 5% palladium on carbon catalyst (1 g). The catalyst was filtered off and washed with ethylacetate. The filtrate was extracted with water by addition of dilute hydrochloric acid until the pH reached 3.0. The aqueous phase was separated and freeze-dried to give the hydrochloride of 1'-ethoxycarbonyloxymethyl 7-(D-α-aminophenylacetamido)-cephalosporanate. The product showed strong IR-absorption at 1780–1750 cm$^{-1}$ indicating the presence of β-lactam ring and ester groups. The product was hydrolysed by human serum to the corresponding cephalosporanic acid.

EXAMPLE 4

7-(2-thienylacetamidoceph-3-em-3-ylmethyl)-N,N-dimethyldithio carbamate-ethoxycarbonyloxymethyl ester To a stirred cooled suspension of 7-(2-thienylacetamidoceph-3-em-3-ylmethyl)-NN-dimethyldithiocarbamate sodium salt (0.5 g, 1 mmole) in 5 ml of dimethyl sulphoxide was added ethylchloromethylcarbonate (1.4 g, 10 mmole) during 15 minutes. After stirring at room temperature over night the mixture was poured into 50 ml of ice-cooled sodiumbicarbonate solution and extracted with 3 × 50 ml of ethylacetate. The combined organic extracts were washed with sodiumbicarbonate solution, water and brine, dried and evaporated in vacuo to give a dark oil, which was washed repeatedly with petrol ether to remove excess of ethylchloromethylcarbonate.

The product was dissolved in 25 ml of chloroform, cooled and stirred while m-chloroperbenzoic acid (0.6 g, 3 mmole) in 15 ml of chloroform was added during 10 minutes. The stirring was continued for 3 hours at room temperature. The mixture was washed with sodiumbicarbonate solution, water and brine, dried and evaporated to give a brownish oil. The product was dissolved in 10 ml of dimethylformamide. Sodium dithionite (0.7 g, 4 mmole) was added and the suspension was cooled while acetylchloride (0.4 g, 5.5 mmole) was added during 10 minutes. The stirring was continued for 30 minutes at room temperature. The mixture was poured into 15 ml of sodium bicarbonate solution, and was extracted with 3 × 15 ml of ethylacetate. The combined organic extracts were washed with sodium bicarbonate solution, water and brine, dried and evaporated in vacuo to give 0.4 g of a dark brownish oil. The product showed strong IR-absorption at 1780–1750 cm$^{-1}$ due to β-lactam and ester carbonyls.

EXAMPLE 5

Ethoxycarbonyloxymethyl 7-(D-α-azidophenylacetamido)-cephalosporanate

Tetrabutylammoniumhydrogensulphate (3.4 g, 10 mmole) was dissolved in 10 ml of 1N sodium hydroxide ice-cooled solution. Potassium 7-(D-α-azidophenylacetamido-cephalosporanate (3.7 g, 10 mmole) and 10 ml of methylenechloride were added. The mixture was shaken and the methylenechloride layer was separated, ethylchloromethylcarbonate (1.4 g, 10 mmole) was added and the mixture was stirred over night at 40°C. The solution was poured into 50 ml of ice-cooled sodium bicarbonate solution and was extracted with 3 × 50 ml of ethylacetate. The combined organic extracts were washed with sodium bicarbonate solution, water and brine, dried and evaporated to give an oil that was repeatedly washed with petroleum ether to give 3.8 g of a brownish gum.

3.0 g of the product was oxidized with m-chloroperbenzoic acid (1.5 g, 8 mmole) in 50 + 25 ml of chloroform in the same way as in example 4. The product came out as 3.3 g of a dark brown oil.

All product was reduced in the same way as in example 4 with sodium dithionite (3.3 g, 13 mmole) in 30 ml of dimethylformamide and acetylchloride (1.2 ml, 17 mmole) to give title product as 2.0 g of a dark brown oil.

1.0 g of the product was dissolved in a minimum amount of benzene and was chromatographed with gradient elution technique on a silica gel column (100 g) using isopropylether-aceton 1:1 mixture as the second solvent. The desired compound was isolated as a brownish foam (0.1 g) from the middle fraction. The product was identical (IR, rate of hydrolyses) with that of example 2.

In the same way cyclopropyloxycarbonyloxyethyl-7-(m-fluoro-azidophenylacetamido)-cephalosporanate could be prepared.

EXAMPLE 6

Methoxycarbonyloxymethyl 7-(enanthamido)-cephalosporanate

In the same way as in example 5 title product was synthesized from potassium 7-(enanthamido)-cephalosporanate (4.2 g, 10 mmole) and methylchloromethyl carbonate (1.2 g, 10 mmole). After oxidation and reduction as in example 5 title product came out as 2.6 g of a brown solid foam. The product showed strong IR-absorption at 1780–1730 cm$^{-1}$ due to β-lactam and ester carbonyls.

EXAMPLE 7

α-azidoethoxycarbonyloxymethyl 7-(phenylacetamido)cephalosporanate

To an ice-cooled suspension of potassium 7-(phenylacetamido) cephalosporanate (4.2 g, 10 mmole) in 10 ml of dimethyl sulphoxide was added α-azidoethyl chloromethylcarbonate (1.8 g, 10 mmole) during 15 minutes. The stirring was continued over night at room temperature. The suspension was poured into 50 ml of ice-cooled sodium bicarbonate solution and was extracted with 3 × 50 ml of ethylacetate. The combined organic extracts were washed with sodium bicarbonate solution, water and brine, dried and evaporated in vacuo to give 3.8 g of a brown oil, that was repeatedly treated with petroleum ether to remove unreacted α-azidoethylchloromethyl carbonate. The resulting gum was dissolved in 75 ml of chloroform. To the cooled solution was added 90% m-chloroperbenzoic acid (1.7 g, 10 mmole) in 50 ml of chloroform during 10 minutes. The stirring was continued for 3 hours at room temperature. The solution was washed with sodium bicarbonate solution and brine, dried and evaporated to give 2.7 g of a yellow oil. The oil was dissolved in 25 ml of dimethylformamide. Sodium dithionite (2.4 g, 10 mmole) was added. The suspension was cooled, stirred while (1.1 g, 15 mmole) of acetylchloride was added during 10 minutes. The stirring was continued for 30 minutes at room temperature. The solution was poured into 50 ml of ice-cooled sodiumbicarbonate solution and extracted with 3 × 50 ml of ethylacetate. The combined organic extracts were washed with sodium bicarbonate solution, water and brine, dried and evaporated to give title product as 2.9 g of a yellow oil that partly crystallized on standing. The product showed strong IR-absorption at 2100 cm$^{-1}$ due to azido groups and at 1780–1740 cm$^{-1}$ due to $\beta$-lactam and ester carbonyls.

The product could be hydrogenated to $\alpha$-aminoethoxycarbonyloxymethyl-7(phenylacetamido)cephalosporanate with 5% palladium on carbon catalyst in the same way as in example 3.

EXAMPLE 8

7($\alpha$-hydroxy-phenylacetamido)-3-(5-methylthiodiazolyl)thiomethyl)cephem, ethoxycarbonyloxymethylester In the same way as in example 1 title product was synthesized in 10 ml of dimethylformamide from 7-($\alpha$-hydroxyphenylacetamide) 3-(2'-methylthiodiazoly-thiomethyl)-3-cephem (0.7 g, 2 mmole) and ethylchloromethylcarbonate (1.4 g, 10 mmole). The oil was oxidized and reduced as in example 1 to give title produce as 0.4 g of a solid brownish foam. The product showed strong IR-absorption at 1780–1740 cm$^{-1}$ due to $\beta$-lactam and ester carbonyls.

EXAMPLE 9

1'-ethoxycarbonyloxyethyl-7-(2-thienylactamido)-cephalosporanate a. In the same way as in example 1 title product was synthesized in 25 ml of dimethylformamide from sodium 7-(2-thienylacetamido)cephalosporanate (2.5 g, 6 mmole) and $\alpha$-chlorodiethylcarbonate (1.8 g, 12 mmole). The oil was oxidized and reduced as in example 1 to give title product as 0.6 of a brown oil that partly crystallized. The product showed strong IR-absorpiton at 1800–1740 cm$^{-1}$ due to $\beta$-lactam and ester carbonyls.

The product was found to be rapidly hydrolysed in presence of human serum.

b. To a stirred and ice-cooled suspension of sodium 7-(2-thienylacetamido)-cephalosporanate (4.18 g, 10 mmole) and sodium bicarbonate (1.68 g, 20 mmole) in 50% dioxane (15 ml) was added $\alpha$-chlorodiethylcarbonate (3.0 g, 20 mmole) in one portion. Stirring was continued at room temperature for 48 hours. The precipitate was filtered off, washed with dioxane (2 × 10 ml) and the filtrate was evaporated in vacuo. The residue dissolved in ethylacetate to (50 ml), the mixture was washed successively with saturated sodium bicarbonate and sodium chloride solution, dried and evaporated. The residue (2.58 g) was dissolved in a minimum amount of benzene and was chromatographed with gradient elution technique on a short silica gel column (30 g) using isopropylether-acetone (7:3) mixture as the second solvent. From the second part of the eluate the ester (1.12 g, 21.9%) was isolated. The infrared (IR) spectrum of the substance (KBr disc) showed strong absorption maximum (cm$^{-1}$) at 1785–1750 ($\beta$-lactam and ester) and 1675 (amide).

The product was oxidized and reduced as in example 1 to give 1'-ethoxycarbonyloxyethyl 7-(2-thienylacetamido)-cephalosporanate as an oil (0.3 g). The identity of the product with that of the product obtained under a) above was ascertained by IR.

EXAMPLE 10

7-(tetrazolylacetamido)-3-[(5-methylthiodiazolyl)-thiomethyl] cephem, ethoxycarbonyloxymethyl ester In the same way as in example 1 title product was synthesized in 25 ml of dimethylformamide from 7-(tetrazolylacetamido)-3-[(5-methylthiodiazolyl)-thiomethyl]-cephem, sodium salt (2.0 g, 4.2 mmole) and ethylchloromethylcarbonate (1.7 g, 12 mmole). The oil was oxidized and reduced as in example 1 to give title product as 0.2 g of a brown-gray solid.

The product showed strong IR-absorption at 1795–1770 cm$^{-1}$ due to $\beta$-lactam and ester carbonyls.

The product was found to be rapidly hydrolysed in presence of human serum.

EXAMPLE 11

Ethoxycarbonyloxymethyl 7-(phenylacetamido)-cephalosporanate

In the same way as in example 5 title product was synthesized in 10 ml of methylenechloride from potassium 7-(phenylacetamido)cephalosporanate (3.7 g, 10 mmole) and $\alpha$-chlorodiethylcarbonate (1.5 g, 10 mmole) to give 2.3 g of a brown oil, that was oxidized and reduced as in example 1 to give title product as 1.4 g of a brown oil, that partly crystallized. The product showed strong IR-absorption at 1790–1740 cm$^{-1}$ due to $\beta$-lactam and ester carbonyls.

The product was found to be rapidly hydrolysed in presence of human serum.

In the same way 1'-phenoxycarbonyloxyethyl 7-(2-thienylacetamido)-cephalosporanate, 1'-(2''-azidoethoxy)carbonyloxyethyl 7-(2-thienylacetamido)-cephalosporanate and 1'-cyclopentyloxycarbonyloxyethyl 7-(D-$\alpha$-azidophenylacetamido)-cephalosporanate could be prepared.

EXAMPLE 12

7-(2-thienylacetamido)-3-(4'-methyl-4'-methylpiperazinium-1'-thiocarbonylthiomethyl)-3-cephem-4-carboxylic acid 4-(cyclopentyloxycarbonyloxymethyl ester a. From chloromethylcyclopentylcarbonate (360 mg, 2 mmole) and 7-(2-thienylacetamido)-3-(4'-methylpiperazino-1'-thiocarbonylthiomethyl)-3-cephem-4-carboxylic acid sodium salt (1.1 g, 2 mmole) in dry dimethylformamide (7 ml) according to the description given in example 1, the corresponding piperazino-ester derivate was prepared. The raw product (1.05 g) was carefully chromatographed on a desactivated (IV) silica gel column (45 g) prepared in benzene with gradient elution technique using isopropylether:ethylacetate (6:4) as the second and ethylacetate:isopropanol (8:2) as the third solvent. The required 7-(2-thienylacetamido)-3-(4'-methylpiperazino-1'-thiocarboxylthiomethyl)-3-cephem-4-carboxylic acid 4-(cyclopentyloxycarbonyloxymethyl) ester was collected by a repeated chromatography and was transferred into dry chloroform (3 ml) without evaporation to dryness. An evaporated aliquot was used for the substance quantity determination (38 mg/ml) and for IR: 1805–1760 (β-lactam and ester) and 1695 (amide).

b. To the above prepared solution methyliodide (28 mg) was added and after standing 7 days at room temperature the solution was evaporated and the residue (137 mg) without purification was used in the hydrolytic experiment.

EXAMPLE 13

Ethoxycarbonyloxyethyl 7-(phenylthioacetamido)-cephalosporanate

A.a. To a stirred solution of phosphorous pentachloride (3.35 g, 16 mmole) in dry methylene chloride (50 ml) were added quinoline (4.0 g, 31 mmole) and, after cooling to −40°C, ethoxycarbonyloxyethyl 7-(2-thienylactamido)-cephalosporanate (7.2 g, 14 mmole). After stirring at −40°C for 60 minutes methanol (450 mg, 14 mmole) was added during 5–10 minutes. After a further 60 minutes at −30°C sodium chloride solution (5 g NaCl in 25 ml H$_2$O) was added. The reaction mixture was stirred at 0°C for 15 minutes. After separating, the organic phase was dried and evaporated to dryness. The residue was washed several times with petroleumether and used directly for acylation (5.9 g).

b. To a stirred and ice-cooled mixture of raw ethoxycarbonyloxyethyl 7-aminocephalosporanate (1.1 g, 2.8 mmole) and dry triethylamine (300 mg, 3 mmole) in dry methylene chloride (10 ml) was added dropwise phenylthioacetylchloride (560 mg, 3 mmole) in dry methylene chloride (2 ml). Stirring was continued for 1 hour. The organic phase was washed with 0.05 N hydrochloric acid and sodium chloride solution. After drying the organic phase was evaporated and the brown oil residue (940 mg) was chromatographed on silica gel (35 g) column with isopropylether-acetone (7:3) mixture. The desired compound was isolated as a white foam (315 mg, 20.8%) from one of the middle fractions and showed only one spot on TLC.

IR (KBr): 1780–1755(CDCl$_3$); 7.35(d, C$_6$H$_5$); 6.75(q, OCH(CH$_3$)O); 5.6–5.15(2d, 6−H−7−H); 4.86(d, CCH$_2$O); 4.15(q, OCH$_2$CH$_3$); 3.75(s, SCH$_2$CO); 3.35(d, SCH$_2$C); 2.10(s, COCH$_3$); 1.45–1.15(m, OCH(CH$_3$)O) and OCH$_2$CH$_3$).

The product was hydrolysed by human serum to the corresponding cephalosporanic acid.

In the same way the 7-(α-propargyloxyphenylacetamido), the 7-(3-phenyl-propenamido) and the 7-(5-chlorobutyracetamido)-cephalosporanic acid 4-(1'-ethoxycarbonyloxyethyl)esters could be prepared.

B. To a stirred mixture of ethoxycarbonyloxyethyl 7-(2-thienylacetamido)-cephalosporanate (2.05 g, 4 mmole) in methylene chloride (20 ml) dimethylaniline (1.58 g, 13 mmole) and phosphorous pentachloride (0.92 g, 4.4 mmole) were added at −10°C. The stirring was continued for 5 hours at about −20°C. Then dry methanol (16 ml) was added at −30°C and stirring was further continued for 3 hours at the same temperature.

To the mixture dimethylaniline (3.0 g, 25 mmole) and phenylthioacetylchloride (0.9 g, 4.8 mmole) were added and stirring was continued further 4 hours at −25°C. Then the mixture was poured into a cold, saturated sodium bicarbonate solution, the organic phase was diluted with methylene chloride, washed successively with water, 0.05 N hydrochloric acid, water and dried. After evaporation the residue (1.7 g) was chromatographed similarly as in A and one of the middle fractions, one substance, a white foam was isolated, which on the basis of spectral data was in all respects identical with the compound prepared in this experiment under A.

EXAMPLE 14

Preparation of 7-(phenylacetamido)-3-methyl-3-cephem-4-carboxylic acid 4-(1'-ethoxycarbonyloxyethyl) ester a) To a stirred and ice-cooled solution of 6-(phenylacetamido) penicillanic acid 3-(1'-ethoxycarbonyloxyethyl) ester (13.5 g, 30 mmole; m.p. 108.5°–109.5°C; [α]$_D^{20}$ +109°, c 1% in CHCl$_3$) in dry chloroform (150 ml) was added dropwise 90% m-chloroperbenzoic acid (6.30 g, 33 mmole) in dry chloroform (75 ml) over 20 minutes. Stirring was continued for 3 hours, then the mixture was poured into a cold saturated sodium bicarbonate solution (150 ml), separated, the organic layer was washed with saturated sodium bicarbonate and sodium chloride solution and dried. After evaporation in vacuo the residue (12.7 g) was solved in minimum amount of benzene and was chromatographed on a desactivated (III) silica gel column (250 g, prepared in benzene) with isopropylether-ethylacetate (8:2 and 1:1 respectively) mixture. The required sulphoxide was isolated as an oil (10.5 g, 67.5%) from the middle fraction of the eluate, which crystallized on standing. Recrystallization from methylene chloride -isopropylether afforded an analytical sample, m.p. 124.5°–125.5°C.

IR (KBr): 1790–1770 (β-lactam and ester); 1685 (amide).

NMR (CDCl$_3$): 7.30(s, C$_6$H$_5$); 6.80(q, OCH(CH$_3$)O); 6.15(d, CONH); 5.95(d, C-6); 5.00(d, C-5); 4.60(s, C-3); 4.25 (q, OCH$_2$CH$_3$); 3.60(s, C$_6$H$_5$CH$_2$CO); 1.65 and 1.25(2 s, gem. CH$_3$); 1.55(d, OCH(CH$_3$)O); 1.30(t, OCH$_2$CH$_3$).

b. 6-(phenylacetamido) penicillanic acid 3-(1'-ethoxycarbonyloxyethyl) ester 1-oxide (1.9 g, 4 mmole) was dissolved in dry dimethylformamide (100 ml) containing acetic acid anhydride (2.0 g, 20 mmole). The solution was let through a glass-coil inmersed in a heated oil-bath kept at a constant temperature of 115° at such a rate, that the solution had 7 minutes contact with the heat-transfer system. The cold mixture was poured into 1N potassium bicarbonate solution (900 ml), extracted with ethylacetate (4 × 400 ml), the combined organic phase was washed several times with saturated sodium chloride solution and dried.

After evaporation the residue (1.55 g) was solved in minimum amount of benzene and was chromatographed on desactivated (III-IV) silica gel (75 g), prepared in benzene, with isopropyletherethylacetate (8:2) mixture as the second solvent. Five substances were separated and one of them was identical with the title compound according to the spectral data.

IR(KBr): 1785–1760 ($\beta$-lactam and ester); 1680 (amide).

NMR (CDCl$_3$): 7.32(s, C$_6$H$_5$); 6.80(q, OCH(CH$_3$)O); 5.75(d, 7-H); 4.85(d, 6-H); 4.80(s, 3-H); 4.15(q, CH$_2$CH$_3$); 3.55(s, C$_6$H$_5$CH$_2$); 3.50 and 3.22(2 d, SCH$_2$O); 2.10(s, CCH$_3$); 1.50(d, OCH(CH$_3$)O); 1.25(t, OCH$_2$CH$_3$).

EXAMPLE 15

Pharmaceutical formulations

For preparation of tablets the following compositions were made:

a) 1'-Ethoxycarbonyloxyethyl-7-(D-α-aminophenyl-acetamido)-cephalosporanate — 360 mg
Starch — 100 mg
Magnesium stearate — 10 mg b) Ethoxycarbonyloxymethyl 7-(D-α-azidophenyl-acetamido)-cephalosporanate — 350 mg
Calcium carbonate — 100 mg
Magnesium stearate — 10 mg c) Ethoxycarbonyloxymethyl 7-(D-α-aminophenyl-acetamido)-cephalosporanate — 375 mg
Lactose — 100 mg
Magnesium stearate — 10 mg d) Ethoxycarbonyloxymethyl 7-(2-thienylacetamido)-cephalosporanate — 400 mg
Microcrystalline cellulose (Avicel) — 100 mg
Magnesium stearate — 10 mg e) 1'-Ethoxycarbonyloxyethyl 7-(2-thienylacet-amido)-cephalosporanate — 400 mg
Calcium carbonate — 100 mg
Lactose — 100 mg
Magnesium stearate — 10 mg For filling in capsules the following formulations were made:

f) Ethoxycarbonyloxymethyl 7-(α-hydroxyphenyl-acetamido)3-(2-methyl-thiadiazolyl-thiomethyl)--$\Delta^3$-cephem-4-carboxylate — 350 mg
Magnesium stearate — 5 mg g) 1'-Ethoxycarbonyloxyethyl 7-(D-α-aminophenyl-acetamido)-cephalosporanate — 350 mg
Lactose — 40 mg
Magnesium stearate — 5 mg For oral suspensions the following formulations were prepared:

h) 1'-Ethoxycarbonyloxyethyl 7-phenylacetamido-cephalosporanate — 35 g
Sodium benzoate — 0.48 g
Sodium chloride — 0.75 g
Flavouring agents — 4.7 g
Aerosil — 0.3 g
Antifoam — 0.0375 g
Alkali salts of polysaccharide sulphates — 4.0 g
Sodium saccharinate — 0.4 g
Sorbitol — ad 100 g

We claim:

1. A pharmaceutical composition for the treatment of bacterial infection which comprises, as an active ingredient, an anti-bacterially effective amount of the compound 7-(tetrazolyl-acetamido)-3-[(5-methylthiodiazolyl)-thiomethyl] cephem, ethoxycarbonyloxymethyl ester, or a therapeutically acceptable salt thereof, in a pharmaceutically acceptable carrier;

2. A method for the treatment of infectious diseases caused by bacterial organisms in animal or man comprising administering to a host an anit-bacterially effective amount of a composition containing, as an active ingredient, the compound 7-(tetrazolyl-acetamido)-3[(5-methylthiodiazolyl)-thiomethyl] cephem, ethoxycarbonyloxymethyl ester, or a therapeutically acceptable salt thereof.

* * * * *

UNITED STATES PATENT AND TRADEMARK OFFICE
CERTIFICATE OF CORRECTION

PATENT NO. : 3,935,204   Page 1 of 5
DATED : January 27, 1976
INVENTOR(S) : Sven Erik Dahlen et al.

It is certified that error appears in the above-identified patent and that said Letters Patent are hereby corrected as shown below:

First page, line 3, "$Y^2$" should be -- $Y^1$ --;

Col. 1, line 8, "cephalosporine" should be -- cephalosporins --;

Col. 1, line 15, that portion of the formula reading "$\begin{array}{c}CH\\ \\Y^1\end{array}$" should be -- $\begin{array}{c}CH\\|\\Y^1\end{array}$ --;

and that portion of the formula reading 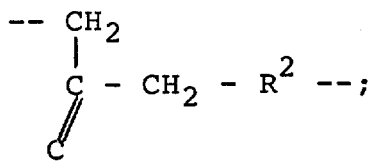 should be

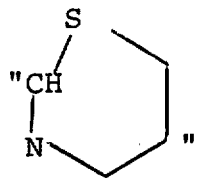 --;

Col. 2, line 52, "aminio" should be -- amino --;

Col. 5, line 2, "intermxied" should be -- intermixed --;

Col. 6, line 27, and heading of Cols. 7-8 and 9-10, that portion of the formula reading

UNITED STATES PATENT AND TRADEMARK OFFICE
CERTIFICATE OF CORRECTION

PATENT NO. : 3,935,204
DATED : January 27, 1976
INVENTOR(S) : Sven Erik Dahlen et al.

It is certified that error appears in the above-identified patent and that said Letters Patent are hereby corrected as shown below:

should be -- 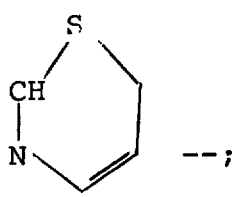 --;

Col. 9, 7th formula in "$R^2$" column,

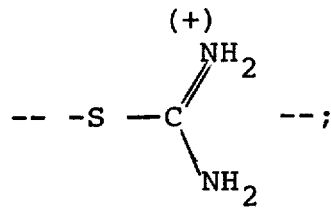 should be

-- -S—C(=NH$_2^{(+)}$)(NH$_2$) --;

Col. 9, 9th and 10th formulas in "$R^2$" column,

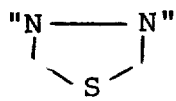 should be

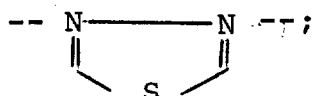 --;

UNITED STATES PATENT AND TRADEMARK OFFICE
CERTIFICATE OF CORRECTION

PATENT NO. : 3,935,204
DATED : January 27, 1976
INVENTOR(S) : Sven Erik Dahlen et al.

It is certified that error appears in the above-identified patent and that said Letters Patent are hereby corrected as shown below:

Col. 11, lines 8-10 and lines 16-18; Col. 12, lines 35-37 and 42-44; Col. 14, lines 45-48, 52-54, and 57-59; and Col. 15, lines 34-36, that portion of the formulas reading "$\begin{array}{c}\text{CH}\\|\\Y^1\end{array}$"  should be $\begin{array}{c}\text{---CH}\\|\\Y^{1'}\end{array}$ --;

Col. 11, line 33, "$R^{3'}$ and $Y^1$" should be -- $R^{3'}$ and $Y^{1'}$ --;

Col. 13, line 47, and Col. 14, line 31,

"$R^3$" should be -- $R^{3'}$ --;

Col. 13, line 59, that portion of the formula reading

"$C-CH_2-R^2$" should be -- $C-CH_2-R^{2'}$ --;

Col. 14, last two lines, "$\overset{|}{C}OOR^3$" should read -- $COOR^3$ --;

Col. 15, line 1, "$R^1$, $R^3$, $X^1$, m, n and $Y^2$" should be -- $R^{1'}$, $R^{3'}$, $X^1$, m, n and $Y^{2'}$ --;

Col. 15, line 24, "$R^3$" (both occurrences) should be -- $R^{3'}$ --;

UNITED STATES PATENT AND TRADEMARK OFFICE
CERTIFICATE OF CORRECTION

PATENT NO. : 3,935,204

DATED : January 27, 1976

INVENTOR(S) : Sven Erik Dahlen et al.

It is certified that error appears in the above-identified patent and that said Letters Patent are hereby corrected as shown below:

<u>Col. 15, line 40</u>, "$R^1$, $X^1$, $Y^1$;" should be -- $R^{1'}$, $X^1$, $Y^{1'}$,--;

<u>Col. 15, lines 47-49</u>, that portion of the formula reading

"-CH- $Y^1$" should be

-- -CH- $|^{1'}$ $Y$   --;  and that portion of the formula reading

" 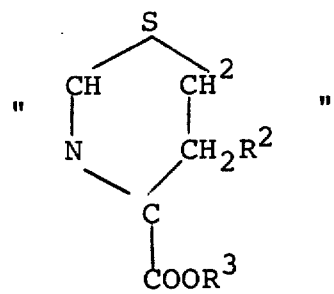 "

should be

-- 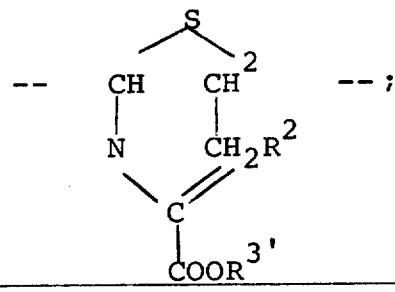 --;

UNITED STATES PATENT AND TRADEMARK OFFICE
CERTIFICATE OF CORRECTION

PATENT NO. : 3,935,204         Page 5 of 5
DATED : January 27, 1976
INVENTOR(S) : Sven Erik Dahlen et al.

It is certified that error appears in the above-identified patent and that said Letters Patent are hereby corrected as shown below:

Col. 18, line 32, "-3/4" should be --10--;
Col. 18, line 47, "$cm^{+1}$" should be --$cm^{-1}$--;
Col. 21, line 46, "absorpiton" should be --absorption--;
Col. 26, line 41, "compount" should be --compound--;
Col. 26, line 45, after "carrier" change ";" to --.--; and
Col. 26, line 48, "anit-" should be --anti- --.

Signed and Sealed this

Seventeenth Day of August 1976

[SEAL]

Attest:

RUTH C. MASON
Attesting Officer

C. MARSHALL DANN
Commissioner of Patents and Trademarks